United States Patent
Chinn et al.

(10) Patent No.: US 6,207,858 B1
(45) Date of Patent: Mar. 27, 2001

(54) REGIOSELECTIVE SYNTHESIS OF DTPA DERIVATIVES

(75) Inventors: Paul Chinn, Vista, CA (US); Albert Gyorkos, Westminister, CO (US); Michael J. LaBarre; Steve Ruhl, both of San Diego, CA (US); Thomas Ryskamp, Poway, CA (US)

(73) Assignee: IDEC Pharmaceuticals Corporation, San Diego, CA (US)

( * ) Notice: Subject to any disclaimer, the term of this patent is extended or adjusted under 35 U.S.C. 154(b) by 0 days.

(21) Appl. No.: 09/261,207

(22) Filed: Mar. 3, 1999

(51) Int. Cl.$^7$ ................................................. C07C 321/00
(52) U.S. Cl. ................................................. 562/426
(58) Field of Search ............................................. 562/426

(56) References Cited

U.S. PATENT DOCUMENTS

| | | | |
|---|---|---|---|
| 4,831,175 | * | 5/1989 | Gansow et al. ........................ 558/17 |
| 5,099,069 | * | 3/1992 | Gansow et al. ........................ 564/368 |
| 5,246,692 | * | 9/1993 | Gansow et al. ........................ 424/1.1 |

OTHER PUBLICATIONS

Synthesis of 1–(p–Isothiocyanatobenzyl) Derivatives of DTPA and EDTA. Antibody Labeling and Tumor–Imaging Studies; *Inorg. Chem.*, 25, pp. 2772–2781; Martin W. Brechbiel et al.; 1986.

Nature of the Bifunctional Chelating Agent Used for Radioimmunotherapy with Yttrium–90 Monoclonal Antibodies: Critical Factors in Determining in Vivo Survival and Organ Toxicity; *Cancer Research*, 49, pp. 2639–2644; Robert W. Kozak et al.; 1989.

Radiometal Labeling of Immunoproteins: Covalent Linkage of 2-(4-Isothiocyanatobenzyl)diethylenetriaminepentaacetic Acid Ligands to Immunoglobulin; *Bioconjugate Chem.*, 1, pp. 59–65; Saed Mirzadeh et al.; 1990.

* cited by examiner

Primary Examiner—Samuel Barts
Assistant Examiner—Brian J. Davis
(74) *Attorney, Agent, or Firm*—Robin L. Teskin

(57) ABSTRACT

The present invention provides a process for high yield regioselective synthesis of DTPA derivatives that eliminates the need for ion exchange chromatographic separation of intermediates. Moreover, as this process yields a single regioisomer of the chelate, it provides for the regiospecific synthesis of desired chelates useful as radiolabeling agents.

29 Claims, 11 Drawing Sheets

REGIOSELECTIVE SYNTHESIS OF DTPA DERIVATIVES

BACKGROUND OF THE INVENTION

1. Field of the Invention

The present invention relates to a process for preparing DTPA derivatives. Particularly, the invention relates to a high yield process for the regiospecific synthesis of DTPA derivatives useful as bi-functional chelators in radioimmunotherapy and imaging.

2. Technology Background

There is an increasing interest in new radio-labeling agents for imaging, tumor detection and immuno therapy, which reduce the various disadvantages presented by conventional agents.

Conventional agents are generally based on radioactive halo-compounds, such as radioactive compounds based on iodine isotopes. However, these agents present a number of limitations. For example, the use of iodine isotopes is greatly limited by the high degradation rate of the carbon-iodine bond, in vivo. Another limitation relates to the less than ideal emission characteristics and physical half-lives of iodine radionuclides. Accordingly, there have been efforts to develop new tumor detection agents to overcome the shortcomings of halogen based radioactive labeling agents.

One avenue for providing more effective imaging and tumor detection agents is offered by organometallic compounds in the form of complex metallic radionuclides. Coupling the imaging and tumor detection agent to the protein is generally achieved through a covalent bond formed between the chelate and the protein by acylation with activated carbonyls, aromatic diazonium coupling, bromoacetyl alkylation or through thiourea bonds.

However, existing organometallic complexes do not provide optimum efficiency for radio labeling and therapy. For example, beyond the choice of a particular radioisotope, successful tumor detection and radioimmunotherapy, also depend on the selection of an effective chelate that joins easily to a particular antibody and allows for radionuclide insertion while preserving the antibody integrity.

Several factors must be considered in designing effective radiometal-chelated antibodies for imaging and tumor detection, and/or immunotherapy. For example, effective radionuclides must be selected according to their physical, chemical and biological properties. An optimal nuclide should be routinely available, easy to couple to the MAb and have an appropriate physical half-life to selectively detect and/or eliminate the target neoplastic tissue while sparing normal tissue.

The MAb that serves to carry the radionuclide to the tumor target must be selected based on the distribution of its antigenic target and on the specificity and binding affinity of the antibody to its target.

Another important aspect to consider in designing effective radiometal-chelated antibodies relates to the choice of the chelating agent (CA) used to couple the radionuclide to the antibodies. For example, effective radiometal-chelated antibodies must be stable in vivo. Stability in vivo depends on the condition that both the chelate linkage and the radiolabeling procedures not alter antibody specificity and bio-distribution.

In addition, selection and synthesis of the chelating agent is critical to optimize the adequacy between the chelate and the selected radionuclide and MAb. In particular, the choice and synthesis of the chelate should avoid inappropriate release of the radionuclide in vivo. This aspect is of paramount importance in that the most common problem associated with conventional chelating agents is their failure to link and securely hold to the antibody. As a consequence, there is considerable dissociation of the radionuclide in vivo from the MAb-CA complex prior to delivery of these agents to the surface of the tumor cell. Accumulation of free toxic radionuclides in normal tissue damages the normal tissue without the benefit of treating and/or detecting the tumor target. Another important aspect relates to the desirability that the selected chelating agent allow the MAb-CA complex to maintain the advantage provided by the specificity of the selected MAb.

Thus, several criteria must be considered in selecting adequate chelates for a selected MAb. For example, (a) addition of the CA should not alter the specificity or the binding affinity of the MAb to the antigenic target; (b) its addition to the MAb should not otherwise damage the antibody and thus alter its rates of catabolism or patterns of tissue distribution; (c) it should hold the radiometal tightly so that there is no premature elution of the radioisotiope from the MAb-CA complex in vivo; (d) linkage to the MAb should not alter the chelate's ability to retain the radionuclide; (e) the mode of linkage to the MAb should be as specific as possible to facilitate the design of protocols for the specific detection and therapy of tumor targets as well as the analysis of the data related to the detection of and treatment of the tumors; and (f) the chelate should be able to help clear the radionuclide following catabolism of the MAb-CA-radionuclide complex.

One group of suitable metal chelates is provided by diethylenetriaminepentaacetic acid (DTPA) and ethylendiaminetetraacetic acid (EDTA) and their derivatives. Chemically modified derivatives of (DTPA) and (EDTA) have been explored as metal ligands capable of effectively chelating radioactive metals, which can be easily coupled to immunoglobulins. However, these reagents were minimally effective due to the reduced affinity for the bound radionuclide, and consequent accumulation of radiochemical compounds in normal tissues.

A number of conventional methods are available for coupling EDTA and DTPA metal complexes to proteins. However, these methods have not reached the high efficiency rates required for effective imaging and tumor detection. For example, conventional methods present a number of disadvantages, such as the need for extensive purification prior to radiolabeling and the deficiency in chelating the metal, resulting from the use of a metal biding site in forming the covalent bond with the protein. Thus, new modes for protein linkage have been studied and new modes, which preserve all metal binding sites have been proposed.

For example, a detailed description of chemically modified ligands that would react rapidly and efficiently with antibody, and which retain the metal for a time that is long compared to the half-lives of radionuclides useful for imaging or therapy is provided by Brechbiel et al in "Synthesis of (1-(p-isothiocyanatobenzyl) derivatives of DTPA and EDTA. Antibody Labeling and Tumor-Imaging Studies." Inorg. Chem. 1986, 25, 2772–2781, the contents of which are incorporated herein by reference in their entirety.

Brechbiel et al propose EDTA and DTPA chemically modified chelates having an isothiocyanate group capable of efficient coupling to proteins. The synthesis of the chelates can be summarized as a "two-step process", wherein the first step includes generating an ethylendiamine or a diethylene triamine followed by alkylation of the amines to form the corresponding polyacetic acid, and the second step includes converting a functional group of the benzyl substitution to obtain a reactive moiety useful for protein coupling.

However, the above "two-step" process for the synthesis of MX-DTPA and the EDTA analog is limited to a low overall yield of less than 2%. The process requires tedious purification of intermediates, which include cation and anion exchange chromatography. In addition, the synthesis produces both regioisomers of MX-DTPA and has shown poor reproducibility.

Thus, there is a need for an alternative synthesis process for preparing DTPA derivatives with a high yield. It is desirable that the new synthesis eliminate the need for ion exchange chromatography in the separation of intermediates, thus providing a process that can be easily scaled up. Further, it is also desirable that such a process produce a single regioisomer of the chelate, thus allowing regiospecific synthesis of desired chelates useful as effective radiolabeling agents.

SUMMARY OF THE INVENTION

The present invention includes a process for preparing DTPA derivatives useful as chelating agents in radioimmuno therapy and imaging. The process of the invention provides a high yield synthesis of DTPA derivatives. In particular, the present invention includes a process for regioselective synthesis of DTPA derivatives suitable for chelating radioactive metals and coupling to immunoglobulins. The process includes coupling a monoprotected diamine and a compound containing an amine and a moiety capable of effectively coupling the DTPA derivative to immunoglobulins or a moiety capable of being converted to effectively couple the DTPA derivative to immunoglobulins.

In one aspect, the present invention provides a process for preparing a DTPA derivative of formula (I)

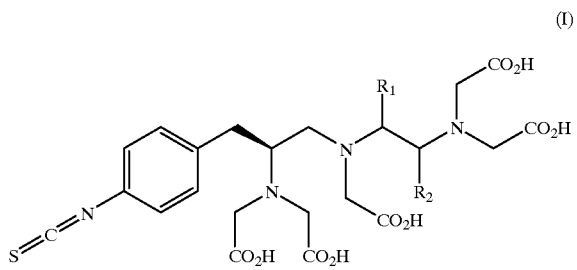

(I)

the process comprising: (a) coupling N-tert-butoxycarbonyl-p-nitro-L-phenylalanine (A) and mono protected diamine (B) to form compound (C); (b) removing the amine protecting groups in (C) to form the TFA-salt (D); (c) reducing (D) to form(E); (d) penta-alkylating (E) to form (F); (e) removing the amine protecting groups in (F) to form the trifluoroacetic acid salt (G); (f) reducing the nitro group in (G) to form the trifluoroacetic acid salt (H); and (g) converting the amino group in (H) to form the DTPA derivative.

The process of the invention allows for synthesizing a variety of DTPA derivatives. Without limiting the scope of the present invention, examples of DTPA derivatives that can be advantageously prepared by the process of the invention include MX-DTPA, 1B3M-DTPA and CHx-DTPA.

According to one aspect, the present invention provides a process for preparation of DTPA derivatives, wherein the nature of the DTPA derivative is determined by the choice of the mono protected diamine (B). R1 and R2 in compound (B) are selected to obtain the desired chemically modified derivative of DTPA.

In another aspect, the present invention provides a process for preparing MX-DTPA comprising: (a) coupling N-tert-butoxycarbonyl-p-nitro-L-phenylalanine (A) and mono-N-tert-butoxycarbonyl protected diamine (B') to form N-(2-N-Tert-butoxycarbonyl-aminopropyl)-N-tert-butoxycarbonyl-p-nitrophenylalaninamide (C'); (b) removing the boc groups in (C') to form N-(2-Aminopropyl)-p-nitrophenylalaninamide TFA-salt (D'); (c) reducing (D') to form 2-Methyl-6-(p-nitrobenzyl)diethylenetriamine trihydrochloride (E'); (d) penta-alkylating (E') to form N,N,N',N",N"-Pentakis[(tert-butoxycarbonyl)methyl]-2-[(4-nitrophenyl)methyl]-6-methyldiethylenetriamine (F'); (e) removing the boc groups in (F') to form N,N,N',N",N"-Pentakis(carboxymethyl)-2-[(4-nitrophenyl)methyl]-6-methyldiethylenetriamine trifluoroacetic acid salt (G'); (f) reducing the nitro group in (G') to form N,N,N',N",N"-Pentakis(carboxymethyl)-2-[(4-aminophenyl)methyl]-6-methyldiethylenetriamine trifluoroacetic acid salt (H'); and (g) converting the amino group in (H') to form 2-(p-Isothiocyanatobenzyl)-6-methyldiethylenetriamine-N,N,N',N",N"-pentaacetic acid (MX-DTPA).

In one aspect, the invention provides a process for synthesizing MX-DTPA, wherein step (a) includes using benzotriazol-1-yloxytris(dimethylamino)phosphonium hexafluorophosphate (BOP) as coupling reagent.

In another aspect, the invention provides a process for synthesizing MX-DTPA, wherein step (a) includes using bis(2-oxo-3oxazolidinyl)phosphinic chloride (BOP—Cl) as coupling reagent.

In yet another aspect, the invention provides a process for synthesizing MX-DTPA, wherein the mono-boc protected diamine (B') is obtained by a process including (i) treating a lactonitrile with ammonium hydroxide to form α-aminonitrile (2); (ii) treating (2) with hydrochloric acid to form the amine hydrochloride salt (3); (iii) protecting the amine with di-tert-butyl dicarbonate to form the boc protected derivative (4); (iv) reducing the nitrile using Raney nickel with a saturated solution of ethanol under two atmospheres of hydrogen to form the mono-boc protected diamine (B').

In still another aspect, the invention provides a process for synthesizing MX-DTPA, wherein the mono-boc protected diamine (B') is obtained by a process comprising (i) alkylating a Schiff Base (5) under phase transfer conditions to form a mono-alkylated product (6); (ii) deprotecting (6) with 1N hydrochloric acid followed by protecting the amine with di-tert-butyl dicarbonate to form the boc protected amine (4); and (iii) reducing (4) with Raney nickel to form the mono-boc protected diamine (B').

In a further aspect, the invention provides a process for synthesizing MX-DTPA, wherein removing the boc groups in (C') to form (D') is performed using trifluoroacetic acid in dichloromethane.

In another aspect, the invention provides a process for synthesizing MX-DTPA, wherein the step of reducing (D') includes treating (D') with borane-tetrahydrofuran complex, followed by treatment with hydrogen chloride to form the triamine hydrochloride salt (E').

In yet another aspect, the invention provides a process for synthesizing MX-DTPA wherein Penta-alkylation of intermediate (E') is performed using acetonitrile and potassium carbonate.

In still another aspect, the invention provides a process for synthesizing MX-DTPA, wherein Penta-alkylation of intermediate (E') is performed using bromo-tert-butylacetate in dimethylformamide and sodium carbonate.

In a further aspect, the invention provides a process for synthesizing MX-DTPA, wherein (F') is purified using column chromatography on silica gel.

In yet another aspect, the invention provides a process for synthesizing MX-DTPA, wherein the step of deprotecting the carboxylic acids in (F') to form the penta-acetic acid derivative (G') is performed using trifluoroacetic acid.

In still another aspect, the invention provides a process for synthesizing MX-DTPA, wherein reducing the nitro group in (G') to form (H') is performed using palladium on carbon under two atmospheres of hydrogen in water.

In yet another aspect, the invention provides a process for synthesizing MX-DTPA, wherein the step of converting (H') into MX-DTPA includes converting the amine (H') to tile isothiocyanate functionality via thiophosgene. The conversion can be conducted in several ways. For example, by (i) adding thiophosgene to a biphasic mixture containing the penta-acetic acid derivative (H) in chloroform and water; (ii) rapidly stirring the mixture for two hours; (iii) removing the solvent under reduced pressure to form a residue; (iv) purifying the residue on reverse phase silica; and (v) eluting with 25% acetonitrile in water containing 1% acetic acid. The conversion can also be performed using dichloromethane and triethylamine, or acetonitrile and sodium bicarbonate or sodium carbonate.

In yet another aspect, the invention provides an improved MX-DTPA composition, wherein the improvement comprises that it substantially only includes a single regioisomer of the chelate. By "substantially only includes" a single regioisomer in the present invention means that the percentage of a single isomer, relative to any other regioisomer is at least 90%, more preferably at least 95%, and most preferably at least 99%.

In still another aspect, the invention is directed to the use of such improved MX-DTPA composition for the production of protein or antibody chelatorand radiolabeled form thereof.

In yet another aspect, the invention is directed to the use of such improved MX-DTPA composition for the production of radiolabeled chelates.

In a further aspect, the invention provides a process for preparing CHx-DTPA comprising: (a) coupling N-tert-butoxycarbonyl-p-nitro-L-phenylalanine (A) and mono protected diamine (B") to form compound (C"); (b) removing the amine protecting groups in (C") to form the TFA-salt (D"); (c) reducing (D") to form (E"); (d) penta-alkylating (E") to form (F"); (e) removing the amine protecting groups in (F") to form the trifluoroacetic acid salt (G"); (f) reducing the nitro group in (G") to form the trifluoroacetic acid salt (H"); and (g) converting the amino group in (H") to form the CHx-DTPA. The mono protected diamine (B") can be used as sys or trans isomer.

DETAILED DESCRIPTION OF THE PREFERRED EMBODIMENTS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The present invention provides a process for high yield regioselective synthesis of chemically modified DTPA derivatives that eliminates the need for ion exchange chromotographic separation of intermediates. Moreover, as this process yields a single regioisomer of the chelate, it provides for the regiospecific synthesis of desired chelates useful as radiolabeling agents.

Figure 1:
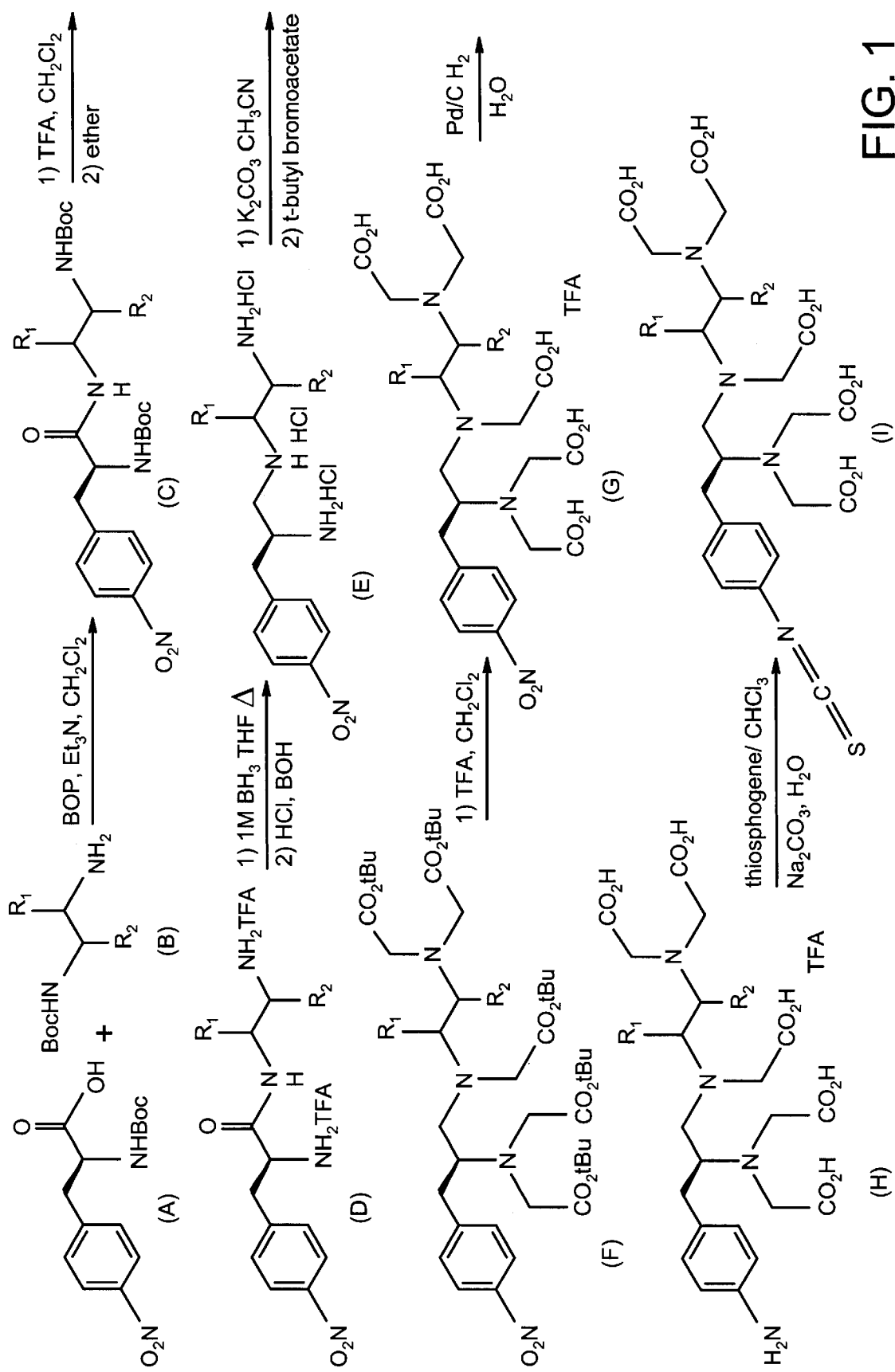
FIG. 1 is a reaction scheme summarizing the seven step process for the regiospecific synthesis of DTPA derivatives of formula (I).

More specifically, FIG. 1 is a reaction scheme summarizing the seven step process for the regiospecific synthesis of DTPA derivatives of formula (I). In this embodiment, the present invention provides a process for preparing a DTPA derivative of formula (I), comprising the steps of: (a) coupling N-tert-butoxycarbonyl-p-nitro-L-phenylalanine (A) and a mono protected diamine (B) to form compound (C); (b) removing the amine protecting groups in (C) to form the TFA-salt (D); (c) reducing (D) to form(E); (d) penta-alkylating (E) to form (F); (e) removing the amine protecting groups in (F) to form the trifluoroacetic acid salt (G); (f) reducing the nitro group in (G) to form the trifluoroacetic acid salt (H); and (g) converting the amino group in (H) to form the DTPA derivative of formula (I).

The process of the invention allows for synthesizing a variety of DTPA derivatives. Without limiting the scope of the invention, examples of DTPA derivatives that can be advantageously prepared by the process of the invention include MX-DTPA, 1B3M-DTPA and CHx-DTPA.

According to one aspect, the present invention provides a process for preparation of DTPA derivatives, wherein the nature of the DTPA derivative is determined by the choice of the mono protected diamine (B). R1 and R2 in compound (B) are selected to obtain the desired chemically modified derivative of DTPA.

Figure 2:
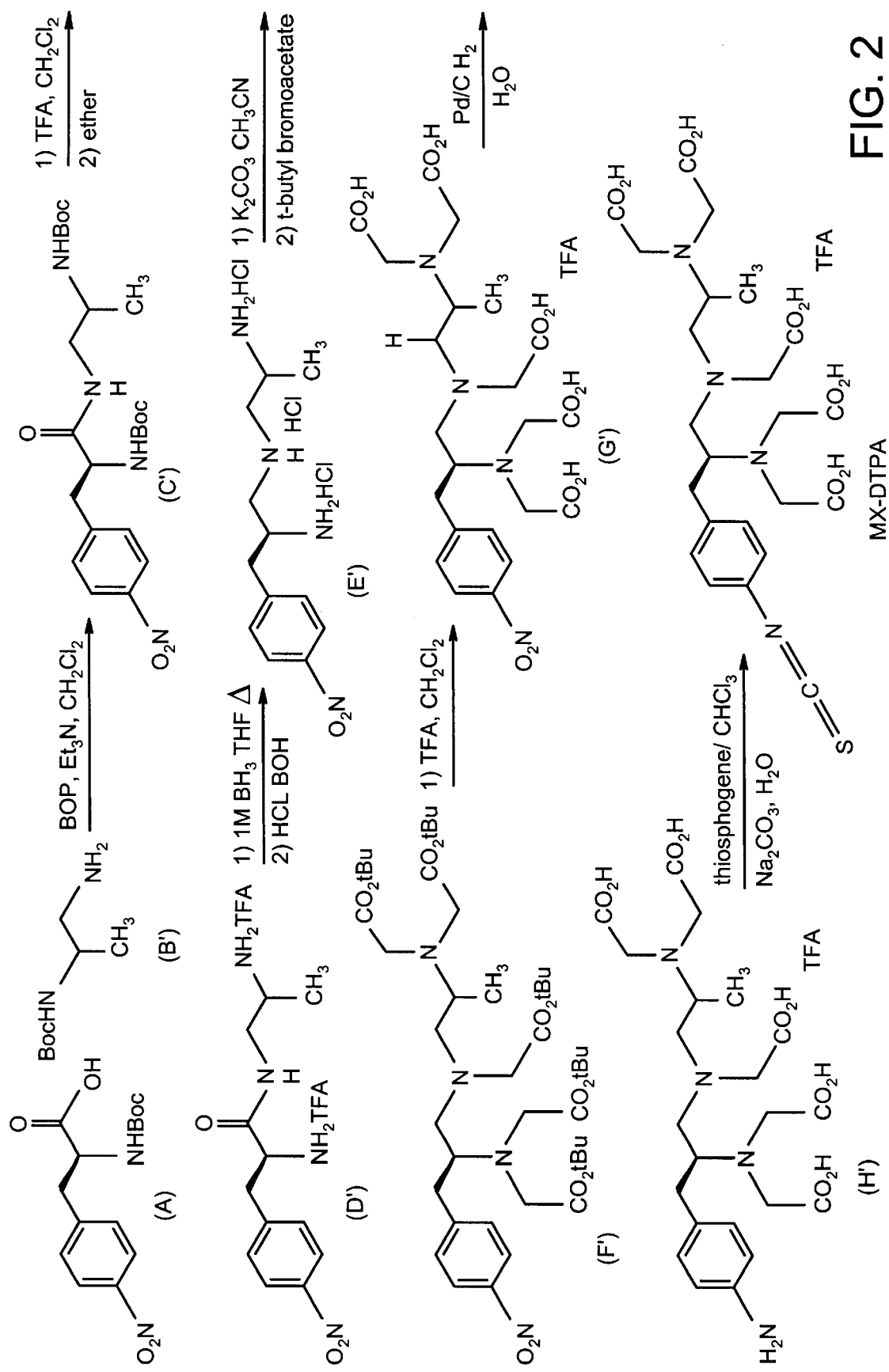
FIG. 2 is a reaction scheme summarizing the seven step process for the regiospecific synthesis of MX-DTPA.

FIG. 2 contains a reaction scheme summarizing the seven-step process for the regiospecific synthesis of MX-DTPA according to one aspect of the invention. In this embodiment, the regioselective synthesis of MX-DTPA is performed in the following steps: (a) coupling N-tert-butoxycarbonyl-p-nitro-L-phenylalanine (A) and mono-N-tert-butoxycarbonyl protected diamine (B') to form N-(2-N-Tert-butoxycarbonyl-aminopropyl)-N-tert-butoxycarbonyl-p-nitrophenylalaninamide (C'); (b) removing the boc groups in (C') to form N-(2-Aminopropyl)-p-nitrophenylalaninamide TFA-salt (D'); (c) reducing (D') to form 2-Methyl-6-(p-nitrobenzyl)diethylenetriamine trihydrochloride (E'); (d) penta-alkylating (E') to form N,N,N', N",N"-Pentakis[(tert-butoxycarbonyl)methyl]-2-[(4-nitrophenyl)methyl]-6-methyldiethylenetriamine (F'); (e) removing the boc groups in (F') to form N,N,N',N",N"-Pentakis(carboxymethyl)-2-[(4-nitrophenyl)methyl]-6-methyldiethylenetriamine trifluoroacetic acid salt (G'); (f) reducing the nitro group in (G') to form N,N,N',N",N"-Pentakis(carboxymethyl)-2-[(4-aminophenyl)methyl]-6-methyldiethylenetriamine trifluoroacetic acid salt (H'); and (g) converting the amino group in (H') to form 2-(p-Isothiocyanatobenzyl)-6-methyldiethylenetriamine-N,N,N',N",N"-pentaacetic acid (MX-DTPA).

The process for the regiospecific synthesis of MX-DTPA has an overall yield of approximately 20% starting from the mono-boc protected diamine (B') and boc-p-nitro-L-phenylalanine (A) and is amenable to scale-up. Thus, synthesizing MX-DTPA according to the invention allows for achieving overall synthesis yields about one order of magnitude higher than the overall yield obtained with the previous process (less than 2%). Further, previous synthesis processes necessitate the purification of an intermediate via tedious anion and cation exchange chromatography. In contrast, the process of the invention eliminates this costly purification procedure and provides the target compound in high purity. For example, in the process of the invention, only one normal phase column chromatography and a reverse phase column are required to purify the final compound.

Figure 3:
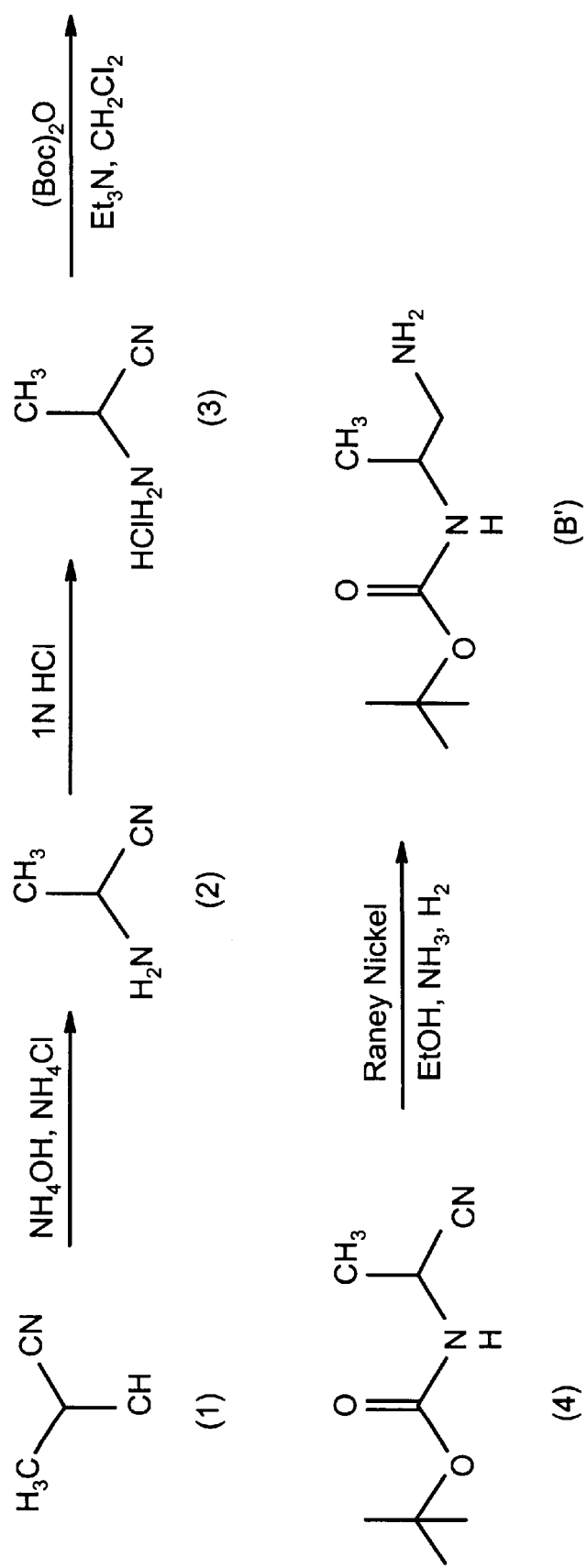
FIG. 3 is a four-step reaction scheme for the synthesis of (B').

FIG. 3 is a four-step reaction scheme for the synthesis of the mono-boc protected diamine (B'). The synthesis of (B') is achieved via treatment of commercially available lactonitrile with ammonium hydroxide to afford the α-aminonitrile (2) which upon treatment with hydrochloric acid provides the amine hydrochloride salt (3). Protection of the amine with di-tert-butyl dicarbonate results in the boc protected derivative (4). Reduction of the nitrile using Raney nickel with a saturated solution of ethanol under two atmospheres of hydrogen produces the requisite mono-boc protected diamine (B'). This reaction sequence is particularly attractive from an economic standpoint because it is reproducible and can be easily amenable to scale-up.

Figure 4:
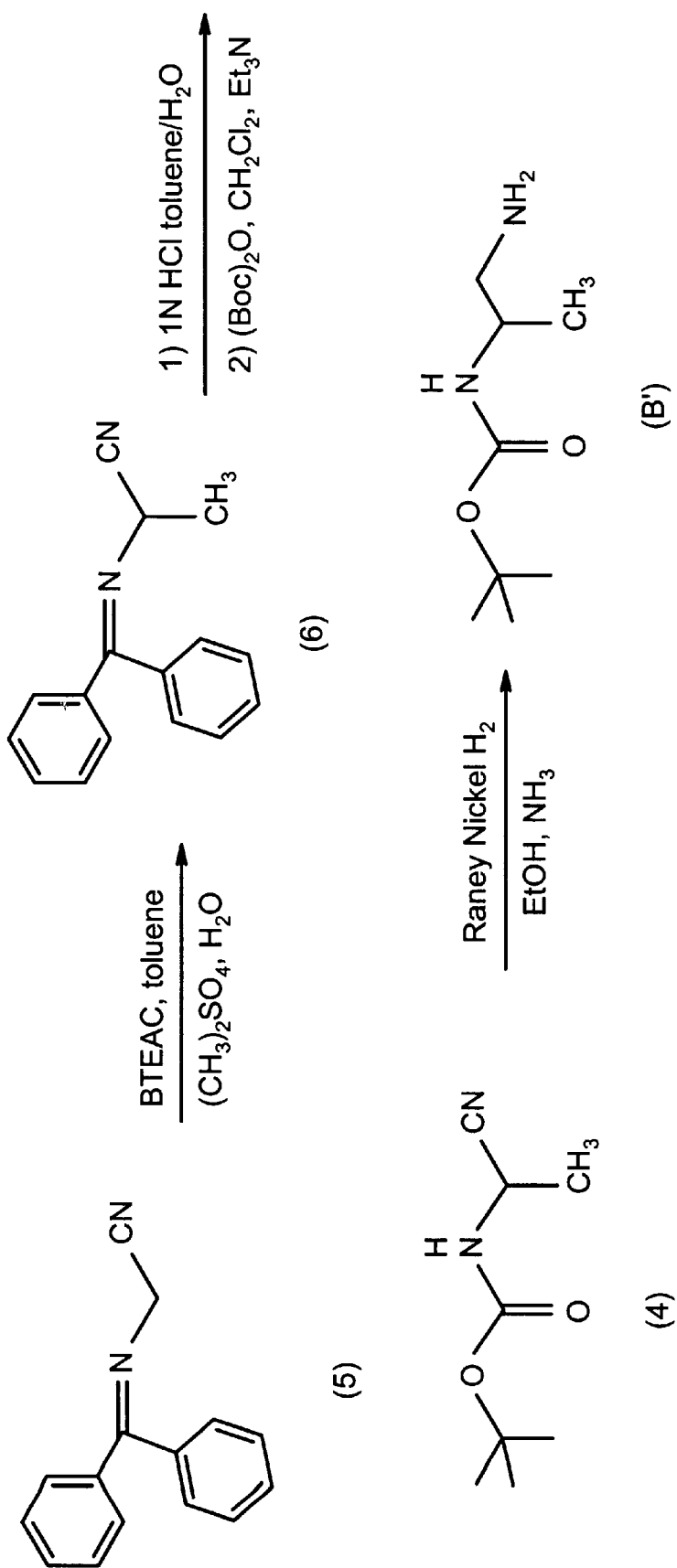
FIG. 4 is an alternative reaction scheme for the synthesis of (B').

Several other conditions for the preparation of (B') were also investigated. For example, FIG. 4 shows a reaction scheme for the synthesis of (B'), wherein (B') is prepared by alkylating a Schiff Base (5) under phase transfer conditions to produce the mono-alkylated product (6) in moderate yield. Deprotection of (6) with 1 N hydrochloric acid followed by protection with di-tert-butyl dicarbonate provides the boc protected amine (4) which upon reduction with Raney nickel produces the requisite mono-boc protected diamine (B').

In the embodiment shown in FIG. 1, the synthesis employs N-tert-butoxycarbonyl-p-nitro-L-phenylalanine (A) which is coupled to the mono-N-tert-butoxycarbonyl protected diamine (B'). The preferred coupling reagent for carrying out this step is benzotriazol-1-yloxytris (dimethylamino)phosphonium hexafluorophosphate (BOP). These conditions allow the synthesis of compound (C') in an isolated yield ranging from 72 to 83%. Purification of (C') can be achieved via acid/base wash followed by trituration with hexanes.

Figure 5:
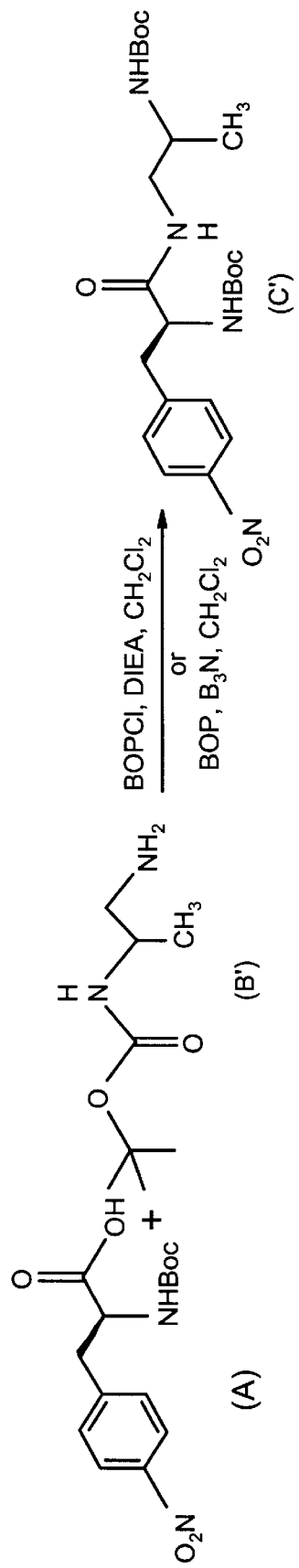
FIG. 5 is a reaction scheme for an alternative step 1 in the reaction scheme of FIG. 2.

FIG. 5 is a reaction scheme representing an alternative step 1 in the reaction scheme of FIG. 2. As shown in FIG. 5, use of bis(2-oxo-3oxazolidinyl)phosphinic chloride (BOP—Cl) also results in the formation of the desired product (C'); however, the yield for this reaction is 23% compared to the yield of 83% which can be achieved with step 1 according to FIG. 2.

Figure 6:
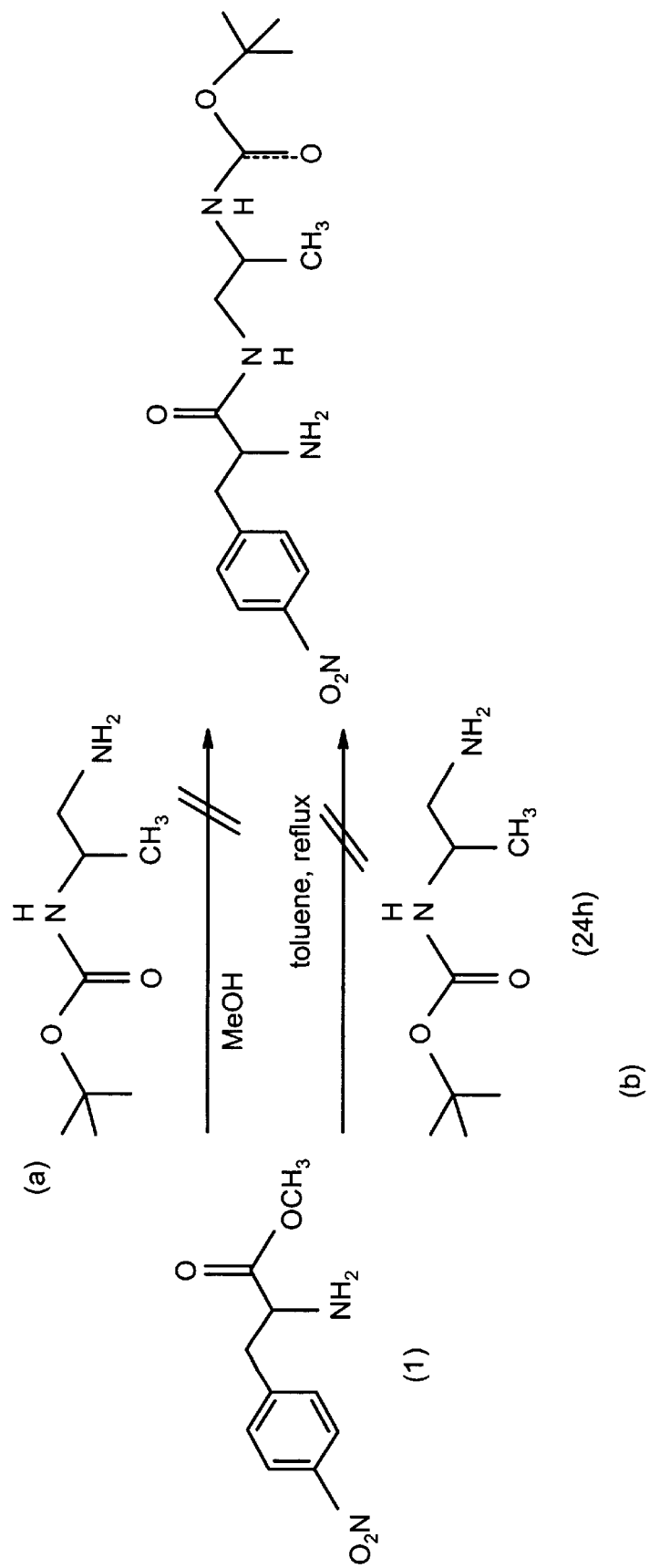
FIG. 6 is a reaction scheme representing unsuccessful condensation of (B') with 4-nitro-L-phenylalanine methyl ester (a) in methanol and (b) in toluene.

Other reaction paths for the synthesis of (C') were unsuccessful. For example, as shown, schematically, in FIG. 6, efforts to generate a related derivative of (C') via direct condensation of (B') with 4-nitro-L-phenylalanine methyl ester (1) either by (a) stirring in methanol or (b) heating at reflux in toluene were not successful.

Having achieved a viable synthesis of compound (C'), the boc protecting groups can then be removed using trifluoroacetic acid in dichloromethane to form the diamine (D'). In this process, (D') is produced in quantitative yield (100%) as a solid.

Figure 7:
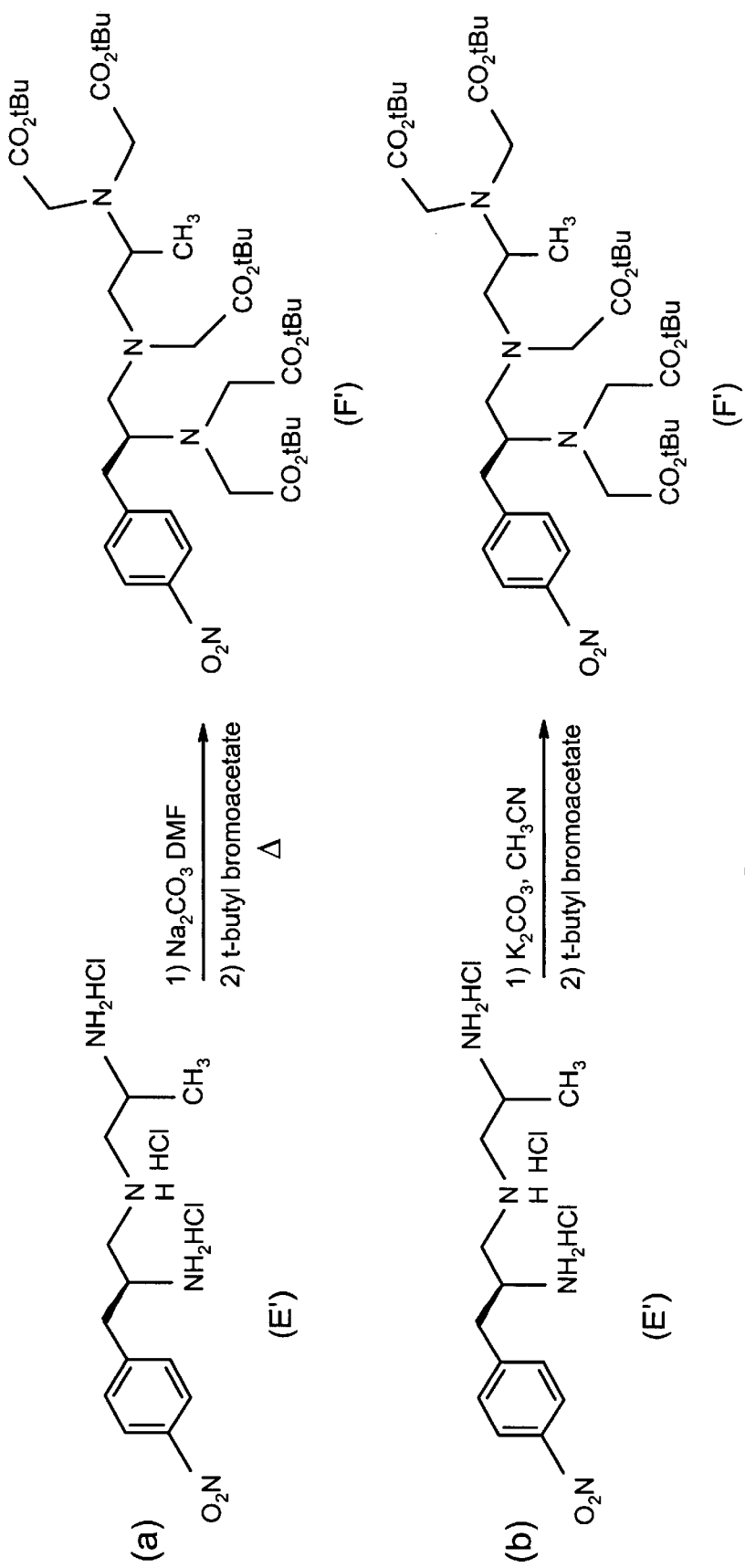
FIG. 7 shows two alternative reaction schemes (a) and (b) for the alkylation of (E') to form (F').

As depicted in FIG. 2, reduction of the amide (D') with a borane-tetrahydrofuran complex, followed by treatment with hydrogen chloride produces the triamine hydrochloride salt (E'). In addition to the alkylation step depicted in FIG. 2, other reaction pathways can be used. For example, FIG. 7 shows two reaction schemes (a) and (b) for the alkylation of (E') to form (F'). Penta-alkylation of intermediate (E') can be achieved using bromo-tert-butylacetate in dimethylformamide and sodium carbonate as base or alternatively using acetonitrile as solvent and potassium carbonate. The latter conditions are more conducive to scale-up and eliminate the use of dimethylformamide which is generally difficult to remove. The isolated yield for this step is in the range of 60% when the reaction is allowed to proceed for 72 to 96 hours. Purification of (F') is preferably performed via column chromatography on silica gel.

As shown, schematically in FIG. 2, the penta-acetic acid derivative (G') can be obtained by deprotecting the carboxylic acids, preferably by using trifluoroacetic acid. Reduction of the nitro group is accomplished using palladium on carbon under two atmospheres of hydrogen in water. It should be noted here that the inventors have avoided the shortcomings of previously known synthesis processes. For example, the invention avoids using ammonium hydroxide, which is difficult to remove, and complicates the synthesis process by requiring a step for generating the isothiocyanate due to the formation of a thiourea by-product.

The final step in the reaction scheme of FIG. 2 relates to converting the amine to tile isothiocyanate functionality via thiophosgene. In this regard, the inventors have investigated various operating conditions.

The preferred conditions for converting (H') into MX-DTPA are depicted in the last step of the scheme of FIG. 2. These conditions include adding thiophosgene to a bi-phasic mixture containing the penta-acetic acid derivative (H') in chloroform and water and rapidly stirring the mixture for two hours. Removal of solvent under reduced pressure followed by purification of the residue on reverse phase silica and eluting with 25% acetonitrile in water containing 1% acetic acid produced the target compound MX-DTPA in good yield.

Figure 8:
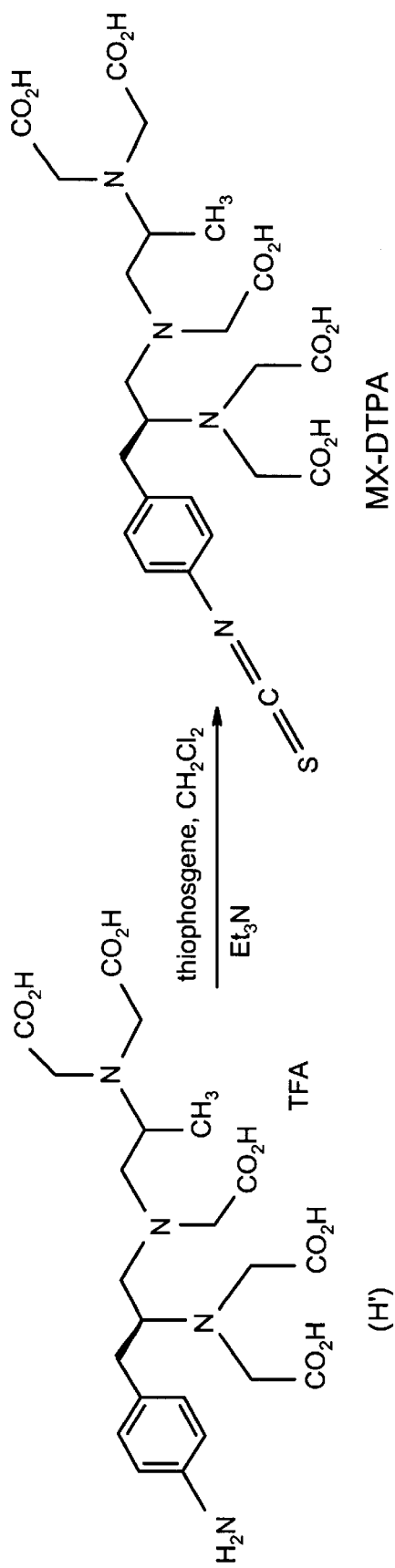
FIG. 8 is an alternative reaction scheme for the conversion of (H') into MX-DTPA.

Other operating conditions have also been investigated. For example, FIG. 8 shows a reaction scheme for the conversion of (H') into MX-DTPA using dichloromethane as solvent and triethylamine as a base. However, in addition to MX-DTPA, the reaction also produces triethylamine hydrochloride as a by-product which could not be removed easily.

Conversion of (H') into MX-DTPA can also be performed using acetonitrile as solvent and sodium bicarbonate or sodium carbonate as base. This reaction also produced other impurities.

MX-DTPA synthesized according to the invention can be effectively used in numerous applications requiring a chelator. For example, MX-DTPA obtained by the process of the invention provides effective radiolabeled chelators, antibody chelators and protein chelators. Radiolabeled MX-DTPA provides an effective tool for numerous applications, such as scintigraphy, radiotherapy and radioimmunoassy.

In this regard, the process for the synthesis of MX-DTPA according to the invention presents numerous advantages. For example, the process does not require cation and anion exchange chromatography necessary for the tedious purification of intermediates. Avoiding the need for cation and anion exchange chromatography provides a process that can be easily scaled up.

Another advantage relates to the high yield afforded by the process of the invention. As discussed above, chelates effective for use in radioimmunoassays must be easily available in quantities sufficient to satisfy a potentially high demand. The process of the invention can provide MX-DTPA with a yield as high as 20%, one order of magnitude higher than existing processes for synthesizing MX-DTPA.

The MX-DTPA chelates synthesized by the process of the invention have high purity. Providing the chelate in a pure form provides numerous advantages, such as easier conditioning and preparation of chelated MAbs, wherein the presence of undesirable by-products is minimized. Minimizing the impurities in the synthesized chelates allows easier conditioning of the chelate for biological applications.

A further advantage relates to the regiospecificity obtained with the process of the invention. The invention provides a novel pathway for the regiospecific synthesis of MX-DTPA.

While not wishing to be bound by any theory, regiospecific synthesis of MX-DTPA according to the invention can be obtained by using compound (A) in the form of a single isomer. Once a particular isomer of compound (A) is selected for starting the synthesis process, the configuration around the chiral carbon in (A) is maintained through out the synthesis process.

Using MX-DTPA in the form of a single regioisomer presents several advantages. For example, using a single isomer of MX-DTPA provides better scintigraphy results and avoids the loss of optic signal associated with the use of racimic mixtures. Also, using a single isomer allows for the design of MAb-CA complexes with high specificity. In this regard, using a single isomer allows all chelate molecules to be linked to the MAb in substantially the same manner.

Another advantage of specifically synthesizing a single regioisomer of MX-DTPA relates to the control provided for the positioning of the chelated radionuclide in relation to the MAb and ultimately to the target tumor. Controlling the positioning of the radionuclide is possible through the use of a single isomer of MX-DTPA. Advantages of providing a single mode of linkage by using a single isomer include the potential improvement in imaging and immunotherapeutic results obtained with the MAb-CA complex.

The MX-DTPA chelate synthesized according to the invention is suitable for chelating a variety of radionuclides. The chelate is also suitable for complexation with a variety of Mabs and proteins. Thus, it is anticipated that the MX-DTPA produced according to the regiospecific synthesis of the invention provides equally effective radiolabeling and therapeutic agents when combined with any radionuclide or MAb suitable for combination with MX-DTPA.

In one embodiment, MX-DTPA is conjugated to 2B8 antibody to form 2B8-MX-DTPA. 2B8 is an anti-CD20 antibody shown to affect B cell depletion upon administration to lymphoma patients. Detailed protocols for forming the 2B8-MX-DTPA are described in detail in U.S. Pat. No. 5,736,137, the contents of which are incorporated herein by reference in their entirety.

However, it should be apparent to those skilled in the art that the MX-DTPA chelators synthesized according to the present invention may be used in the radiolabeling of other anti-CD20 antibodies, or any other antibody which has been conjugated to DTPA or other polyvalent chelator. Also, MX-DPTA chelates produced according to the invention may be attached to other proteins and peptides, e.g., receptors, hormones, growth factors, such as somatostaton peptides.

While the above detailed description focuses on the synthesis of MX-DTPA, the process of the invention is equally applicable to the synthesis of other chemically modified DTPA derivatives. In this regard, the process of the invention can be advantageously used in the regioselective synthesis of a variety of DTPA derivatives suitable for chelating radioactive metals and coupling to immunoglobulins. The process comprises coupling a monoprotected diamine and a compound comprising an amine and a moiety capable of effectively coupling the DTPA derivative to immunoglobulins or a moiety capable of being converted to effectively couple the DTPA derivative to immunoglobulins. As can be easily appreciated by those skilled in the art, the process of the invention is particularly advantageous in that a variety of monoportected diamines can be coupled to a variety of compounds comprising an amine and a moiety capable of effectively coupling the DTPA derivative to immunoglobulins or a moiety capable of being converted to effectively couple the DTPA derivative to immunoglobulins. Synthesis of such DTPA derivatives is within the scope of the present invention.

For example, in one embodiment of the invention, 1B3M-DTPA is prepared according to a reaction scheme similar to the reaction scheme of FIG. 2. 1B3M-DTPA is prepared by using an isomer of (B'), wherein the positions of $R_1$ (i.e., H) and $R_2$ (i.e., $CH_3$) are exchanged.

Figure 9:
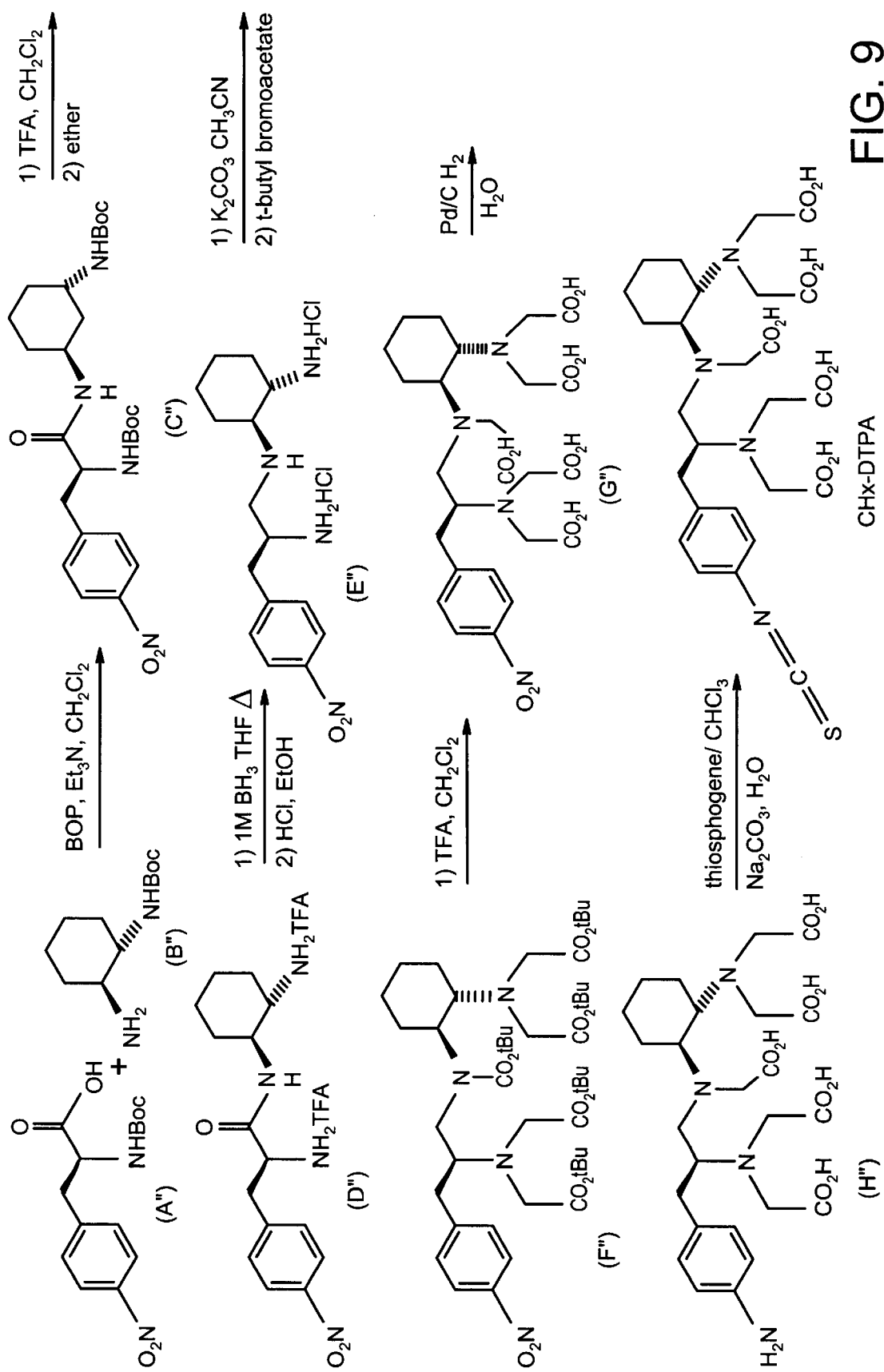
FIG. 9 is a reaction scheme summarizing the seven step process for the regiospecific synthesis of CHx-DTPA.

CHx-DTPA is another example of DTPA derivatives that can be prepared according to the process of the invention. FIG. 9 is a reaction scheme summarizing the process for the synthesis of CHx-DTPA. In step (a) of the scheme of FIG. 9, the mono Boc protected diaminocyclohexane (B") is condensed with compound (A) to form compound (C"). After compound (C") is formed, the synthesis of CHx-DTPA proceeds in steps similar to those of FIG. 2.

Figure 10:
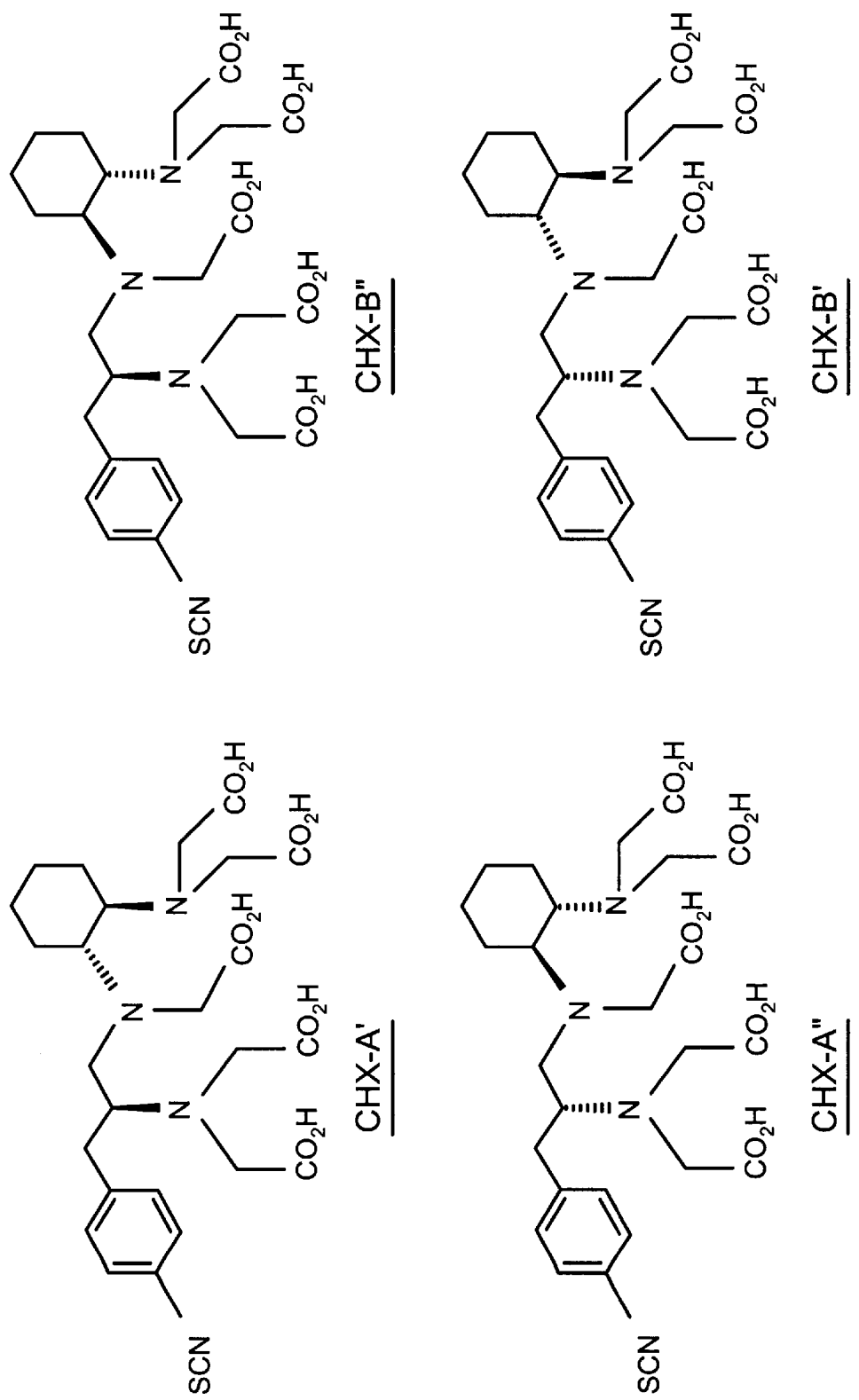
FIG. 10 a scheme depicting the regioisomers of CHx-DTPA selectively prepared by the process of the invention.

The diamine (B") can be used in the sys or trans form to prepare corresponding CHx-DTPA isomers. FIG. 10 depicts the regioisomers of CHx-DTPA which can be prepared by combining selected isomers of compounds (A) and (B").

Figure 11:
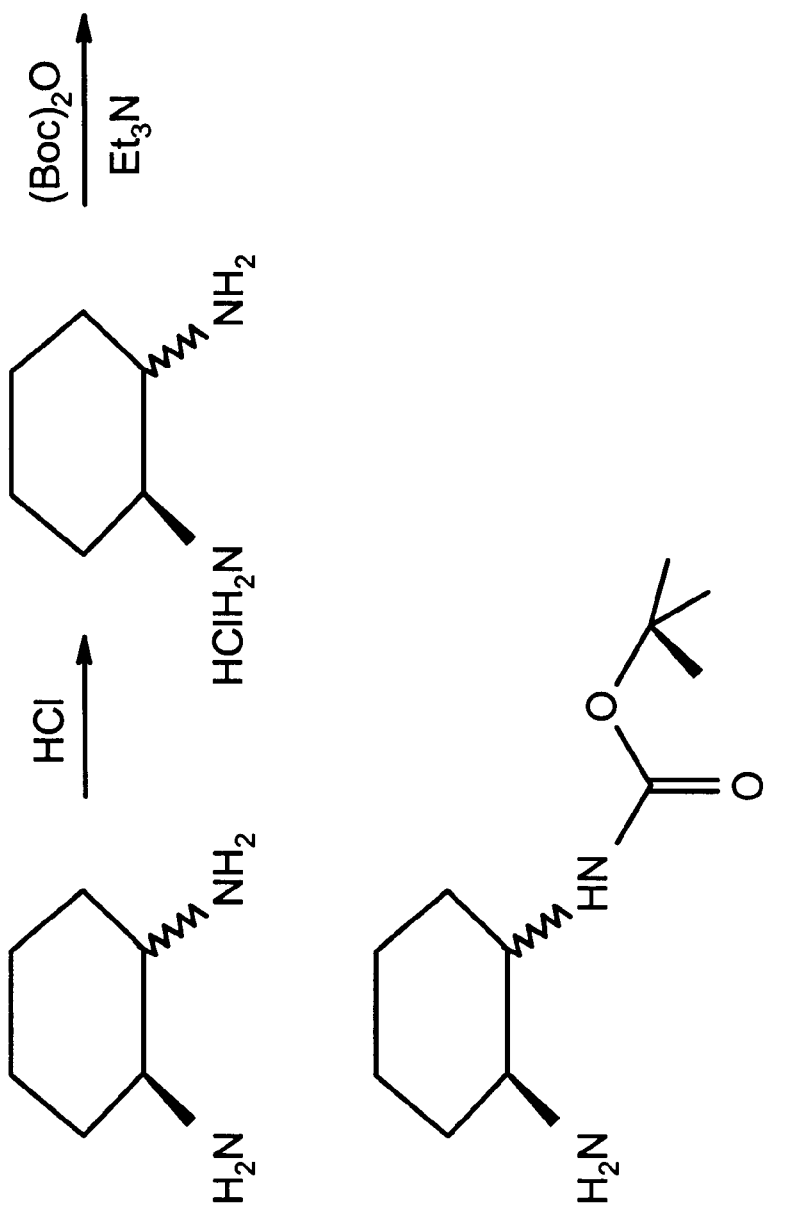
FIG. 11 is a two-step reaction scheme for the synthesis of (B").

The mono protected diamine (B") can be prepared in various ways. A preferred path for preparing (B") is depicted in the two step reaction scheme of FIG. 11.

EXAMPLES

Commercially available reagents and HPLC grade or anhydrous solvents were used without further purification. Normal phase column chromatography and TLC were performed on ICN silica gel (63-200, 60A) and Merck silica gel (60A) with fluorescent indicator respectively. Reverse phase column chromatography and TLC were performed on EM Science LiChroprep RP-18 (40–63 um) and Techware RPS-F reversed phase hydrocarbon impregnated silica gel with fluorescent indicator respectively.

Synthesis of 1-N-tert-butoxycarbonyl-2-methyl-ethylenediamine (B')

a. 2-Amino propanenitrile hydrochloride (3)

A mixture containing 23.1 g (324.99 mmol) of lactonitrile (tech grade 90% purity), 7.1 g (132.74 mmol) of ammonium chloride and 86 ml (2208.3 mmol) of ammonium hydroxide was allowed to stir at room temperature for 2 hours. The reaction was extracted with dichloromethane (2×500 ml) and the organic phase dried over anhydrous magnesium sulfate. The mixture was filtered and the solvent removed under reduced pressure to produce 24 g of a yellow oil (2). The yellow oil was diluted with 250 ml of anhydrous diethyl ether and cooled in an ice bath. Then, 350 ml (350 mmol) of 1 N hydrochloric acid in ether were added. After stirring for 10 minutes, the resultant solid was filtered, washed with ether and dried under vacuum to produce 28.79 product with a yield of 92.83%, based on the purity of starting lactonitrile.

b. N-tert-butoxycarbonyl-2-aminopropanenitrile (4)

To a mixture containing 28.5 g (268.79 mmol) of 2-amino propanenitrile hydrochloride in 300 ml of anhydrous dichloromethane was added 104 ml (746.16 mmol) of triethylamine. The mixture was cooled in an ice bath followed by the addition of 64.5 g (295.53 mmol) of di-tert-butyl dicarbonate in 100 ml of anhydrous dichloromethane over 30 minutes. The reaction was allowed to warm to room temperature under stirring for 48 hours. The reaction mixture was filtered through a glass sintered funnel and the filtrate was reduced under reduced pressure. 1 L of diethyl ether was added and the mixture was allowed to stir for 15 minutes. The mixture was again filtered through a glass sintered funnel to remove the remaining triethylamine hydrochloride. The filtrate was concentrated under reduced pressure. Column chromatography of the residue on silica gel eluting with 30% ethylacetate/hexanes produced 18.50 g of product wit a yield of 40.44%.

c. 1-N-tert-butoxycarbonyl-2-methyl-ethylenediamine (B')

To a 500 ml Parr flask was added 18.4 g (108.10 mmol) of N-tert-butoxycarbonyl-2-aminopropanenitrile and 200 ml absolute ethanol saturated with ammonia. Raney nickel was then added, (10 g of a 50% slurry in water) and the flask pressurized to 50 psi hyvdrogen gas and vented. The flask was again pressurized to 50 psi hydrogen gas and vented. Then, the flask was pressurized to 50 psi hydrogen gas and shaken until there was no further uptake of hydrogen, which is generally achieved overnight. The flask was vented and the mixture filtered through a pad of celite 521. The filtrate was concentrated under reduced pressure to produce 19.2 g of product as a colorless oil with quantitative yield (100%).

Alternatively, 2-Amino propanenitrile hydrochloride (3) can be prepared from N-(Diphenylmethylene) aminoacetonitrile as follows a. N-(Diphenylmethylene)-2-methyl-aminoacetonitrile (6)

To a solution containing 50 g (226.98 mmol) of N-(diphenylmethylene)aminoacetonitrile in 250 ml of toluene was added 4.5 g (19.76 mmol) of benzytriethylammonium chloride (BTEAC) followed by addition of 28.3 g (707.50 mmol) of sodium hydroxide in 50 ml of water. The reaction was cooled in an ice bath followed by a dropwise addition of 22 ml (232.51 mmol) of methylsulfate for 1 hour. The reaction was allowed to warm to room temperature over 24 hours. The reaction mixture was diluted with 1 liter of dichloromethane and washed with water (2×1 L). The organic phase was dried over anhydrous magnesium sulfate. Filtration, removal of solvent and column chromatography of the residue on silica gel eluting with 20% ethyl acetate/hexanes produced 46.2 g of product with a yield of 62.05%.

b. 2-Amino propanenitrile hydrochloride (3)

A mixture containing 3.0 g (12.80 mmol) of N-diphenylmethylene)-2-methyl-aminoacetonitrile in 30 ml of hexane and 25 ml (25 mmol) of 1N aqueous hydrochloric acid was allowed to stir at room temperature for 72 hours. The aqueous phase was separated and washed with hexane. Concentration of the aqueous phase under reduced pressure produced 1.25 g of product with a yield of 92.10%.

N-(2-N-Tert-butoxycarbonyl-aminopropyl)-N-tert-butoxycarbonyl-p-nitrophenylalaninamide (C')

To a solution containing 25 g (80.57 mmol) of N-t-boc-p-nitro-L-phenylalanine in 300 ml of anhydrous dichloromethane was added 12.5 ml (89.68 mmol) of triethylamine followed by 37 g (83.66 mmol) of benzotriazol-1-yloxytris (dimethylamino)phosphonium hexafluorophosphate (BOP). After stirring at room temperature for 1 hour, 15.1 g (86.66 mmol) of 1-N-tert-butoxycarbonyl-2-methyl-ethylenediamine in 40 ml of anhydrous dichloromethane were added. The reaction was allowed to stir at room temperature for 20 hours. The reaction mixture was diluted with 300 ml of dichloromethane and washed with 1N aqueous hydrochloric acid (2×500 ml), saturated aqueous sodium bicarbonate (2×500 ml) and water (1×500 ml). The organic phase was dried over anhydrous magnesium sulfate. Filtration and removal of solvent under reduced pressure produced a yellow solid. Hexanes were then added (600 ml) and the mixture allowed to stir for 20 minutes. The solid was filtered and dried to yield 27.0 g (71.83%) of product as a white solid.

N-(2-Aminopropyl)-p-nitrophenylalaninamide TFA-salt (D')

To a solution containing 26.50 g (56.80 mmol) of N-(2-N-Tert-butoxycarbonyl-aminopropyl)-N-tert-butoxycarbonyl-p-nitrophenylalaninamide in 300 ml of dichloromethane was added 65 ml (843.77 mmol) of trifluoroacetic acid. The reaction was allowed to stir at room temperature for 1 hour. The solvent was removed under reduced pressure followed by the addition of 500 ml of anhydrous diethyl ether. The resultant solid was filtered through a glass sintered funnel and washed with 400 ml of diethyl ether. The solid was dried under vacuum to afford 32.0 g (100%) of product containing some residual trifluoroacetic acid and diethyl ether. The material is used without further purification.

2-Methyl-6-(p-nitrobenzyl)diethylenetriamine trihydrochloride (E')

To a solution containing 35 g (70.80 mmol) of N-(2-aminopropyl)-p-nitrophenylalaninamide TFA salt in 500 ml of anhydrous tetrahydrofuran was added 500 ml of 1M borane-tetrahydrofuran complex over 30 minutes. The reaction was heated at reflux for 16 hours. After cooling the reaction in an ice-bath, 122 ml of methanol were added slowly to quench the excess borane reagent. After complete gas evolution, the solvent was removed under reduced pressure. The residue was taken up in 265 ml of absolute ethanol and the solution was saturated with hydrochloric acid (g) while being cooled in an ice-bath. The mixture was then diluted with 200 ml of anhydrous diethyl ether and the resultant solid filtered and dried under vacuum to produce 19.39 g of product with a yield of 75.72%.

N,N,N',N'',N''-Pentakis[(tert-butoxycarbonyl) methyl]-2-[(4-nitrophenyl)methyl]-6-methyldiethylenetriamine (F')

To a mixture containing 19.0 g (52.53 mmol) of 2-methyl-64 p-nitrobenzyl)diethylenetriamine trihydrochloride in 550 ml of anhydrous acetonitrile was added 86.60 g (626.58 mmol) of potassium carbonate followed by 42 ml (284.44 mmol) of tert-butyl bromoacetate. After stirring at room temperature for 90 h, the reaction was diluted with 500 ml of water and extracted with ethyl acetate (2×500 ml). The organic phase was dried over anhdrous magnesium sulfate. Filtration and removal of solvent under reduced pressure gave a yellow oil. Column chromatography of this oil on silica gel eluting with 30% ethyl acetate/hexanes produced 26.37 g of product wit a yield of 60.99%.

N,N,N',N'',N''-Pentakis(carboxymethyl)-2-[(4-nitrophenyl)methyl]-6-methyldiethylenetriamine trifluoroacetic acid salt (G')

A solution containing 5.0 g (6.08 mmol) of N,N,N',N'',N''-pentakis[(tert-butoxycarbonyl)methyl]-2-[(4-nitrophenyl)methyl]-6-methyldiethylenetriamine in 35 ml of trifluoroacetic acid was allowed to stir at room temperature for 48 h. The solvent was removed under reduced pressure and the resultant solid dried under vacuum to produce 4.02 g of product as a pale yellow solid with a yield of 74.75%.

N,N,N',N'',N''-Pentakis(carboxymethyl)-2-[(4-aminophenyl)methyl]-6-methyldiethylenetriamine trifluoroacetic acid salt (H')

To a Parr flask was added 3.40 g (3.84 mmol) of N,N,N',N'',N''-Pentakis(carboxymethyl)-2-[(4-nitrophenyl)methyl-]-6-methyldiethylenetriamine trifluoroacetic acid salt and 50 ml of water followed by the addition of 0.3 g of 5% palladium on carbon. The flask was pressurized to 30 psi hydrogen and vented twice. The vessel was then pressurized to 45 psi hydrogen and shaken. Once hydrogen uptake ceased, typically after 2 to 4 hours, the flask was vented and the mixture filtered through a pad of celite. The celite was washed with 20 ml of water. The filtrate was concentrated under reduced pressure to afford 3.02 g of product with a yield of 92.03%. The spectral data obtained for this product are consistent with those of a reference standard.

2-(p-Isothiocyanatobenzyl)-6-methyldiethylenetriamine-N,N,N',N'',N''-pentaacetic acid (MX-DTPA)

In a 1 L round bottom flask equipped with a magnetic stir, 7.0 g (7.23 mmol) of N,N,N',N'',N''-Pentakis(carboxvmethyl)-2-[(4-aminophenyl)methyl]-6-methyldiethylenetriamine trifluoroacetic acid salt were added to a mixture containing 150 ml of water and 300 ml of chloroform, followed by 4.67 g (44.06 mmol) of sodium carbonate. The resulting solution had a pH of approximately 9.0. To this biphasic mixture was added 0.64 ml (8.39 mmol) of thiophosgene and the solution allowed to stir at room temperature for 2 hours. The solvent was removed under reduced pressure to form a residue. The residue was dissolved in 15 ml of 1% acetic acid in water and placed on a reverse phase silica gel column eluting with 1% acetic acid followed by 25% acetonitrile/water containing 1% acetic acid. The fractions containing the product were pooled and the solvent removed under reduced pressure to produce 2.47 g of product as a pale yellow solid in a yield of 61.60%.

While the invention has been described in terms of preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A process for regioselective synthesis of a DTPA derivative suitable for chelating radioactive metals and coupling to immunoglobulins, the process comprising regioselectively coupling:
   (a) a monoprotected diamine; and
   (b) a compound comprising an amine and a moiety capable of effectively coupling the DTPA derivative to immunoglobulins or a compound comprising an amine and a moiety capable of being converted for effectively coupling the DTPA derivative to immunoglobulins;
   thereby synthesizing a substantially isomerically pure DTPA derivative.

2. A process for preparing a DTPA derivative of formula (I)

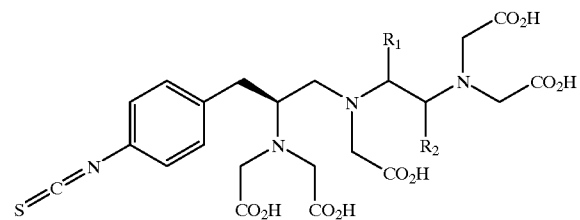

wherein $R_1$ and $R_2$ are selected to provide a desired DTPA derivative, the process comprising:
   (a) coupling N-tert-butoxycarbonyl-p-nitro-L-phenylalanine (A) and mono protected diamine (B) to form compound (C);
   (b) removing the amine protecting groups in (C) to form the TFA-salt (D);
   (c) reducing (D) to form (E);
   (d) penta-akylating (E) to form (F);
   (e) removing the amine protecting groups in (F) to form the trifluoroacetic acid salt (G);
   (f) reducing the nitro group in (G) to form the trifluoroacetic acid salt (H); and
   (g) converting the amino group in (H) to form the DTPA derivative of formula (I).

3. The process of claim 2, wherein the compound of formula (I) is MX-DTPA.

4. The process of claim 2, wherein the compound of formula (I) is 1B3M-DTPA.

5. The process of claim 2, wherein the compound of formula (I) is CHx-DTPA.

6. The process of claim 2, wherein the nature of the DTPA derivative is controlled by selecting the diamine (B).

7. A process for preparing MX-DTPA comprising:
   (a) coupling N-tert-butoxycarbonyl-p-nitro-L-phenylalanine (A) and mono-N-tert-butoxycarbonyl protected diamine (B') to form N-(2-N-Tert-butoxycarbonyl-aminopropyl)-N-tert-butoxycarbonyl-p-nitrophenylalaninamide (C');
   (b) removing the boc groups in (C') to form N-(2-Aminopropyl)-p-nitrophenylalaninamide TFA-salt (D');
   (c) reducing (D') to form 2-Methyl-6-(p-nitrobenzyl) diethylenetriamine trihydrochloride (E');
   (d) penta-alkylating (E') to form N,N,N',N'',N''-Pentakis[(tert-butoxycarbonyl)methyl]-2-[(4-nitrophenyl)methyl]-6-methyldiethylenetriamine (F');

(e) removing the boc groups in (F') to form N,N,N',N",N"-Pentakis(carboxymethyl)-2-[(4-nitrophenyl)methyl]-6-methyldiethylenetriamine trifluoroacetic acid salt (G');

(f) reducing the nitro group in (G') to form N,N,N',N",N"-Pentakis(carboxymethyl)-2-[(4-aminophenyl)methyl]-6-methyldiethylenetriamine trifluoroacetic acid salt (H'); and (g) converting the amino group in (H') to form 2-(p-Isothiocyanatobenzyl)-6-methyldiethylenetriamine-N,N,N',N",N"-pentaacetic acid (MX-DTPA).

8. The process of claim 7, wherein (a) comprises using benzotriazol-1-yloxytris(dimethylamino)phosphonium hexafluorophosphate (BOP) as coupling reagent.

9. The process of claim 7, wherein (a) comprises using bis(2-oxo-3oxazolidinyl)phosphinic chloride (BOP—Cl) as coupling reagent.

10. The process of claim 7, wherein the mono-boc protected diamine (B') is obtained by a process comprising (i) treating a lactonitrile with ammonium hydroxide to form α-aminonitrile (2); (ii) treating (2) with hydrochloric acid to form the amine hydrochloride salt (3); (iii) protecting the amine with di-tert-butyl dicarbonate to form the boc protected derivative (4); (iv) reducing the nitrile using Raney nickel with a saturated solution of ethanol under two atmospheres of hydrogen to form the mono-boc protected diamine (B').

11. The process of claim 7, wherein the mono-boc protected diamine (B') was obtained by a process comprising (i) alkylating the Schiff Base (5) under phase transfer conditions to form a mono-alkylated product (6); (ii) deprotecting (6) with 1N hydrochloric acid followed by protecting with di-tert-butyl dicarbonate to form the boc protected amine (4); and (iii) reducing (4) with Raney nickel to form the mono-boc protected diamine (B').

12. The process of claim 7, wherein removing the boc groups in (C') to form (D') is performed using trifluoroacetic acid in dichloromethane.

13. The process of claim 7, wherein the step of reducing (D') comprises treating (D') with borane-tetrahydrofuran complex, followed by treatment with hydrogen chloride to form the triamine hydrochloride salt (E').

14. The process of claim 7, wherein Penta-alkylation of intermediate (E') is performed using acetonitrile and potassium carbonate.

15. The process of claim 7, wherein Penta-alkylation of intermediate (E') is performed using bromo-tert-butylacetate in dimethylformamide and sodium carbonate.

16. The process of claim 7, wherein (F') is purified using column chromatography on silica gel.

17. The process of claim 7, wherein deprotecting the carboxylic acids in (F') to form the penta-acetic acid derivative (G') is performed using trifluoroacetic acid.

18. The process of claim 7, wherein reducing the nitro group in (G') to form (H') is performed using palladium on carbon under two atmospheres of hydrogen in water.

19. The process of claim 7, wherein the step of converting (H') into MX-DTPA comprises using thiophosgene to convert the amine group in (H') to the isothiocyanate functionality in MX-DTPA.

20. The process of claim 14, wherein the step of converting (H') into MX-DTPA comprises: (i) adding thiophosgene to a biphasic mixture containing the penta-acetic acid derivative (H') in chloroform and water; (ii) rapidly stirring the mixture for two hours; (iii) removing the solvent under reduced pressure to form a residue; (iv) purifying the residue on reverse phase silica; and (v) eluting with 25% acetonitrile in water containing 1% acetic acid.

21. The process of claim 19, wherein converting (H') into MX-DTPA comprises using dichloromethane and triethylamine.

22. The process of claim 19, wherein converting (H') into MX-DTPA comprises using acetonitrile and sodium bicarbonate or sodium carbonate.

23. An MX-DTPA composition produced according to the method of claim 7.

24. An improved method of producing an antibody chelator, wherein the improvement comprises linking MX-DTPA produced according to claim 7 to an antibody.

25. A substantially isomerically pure MX-DTPA composition.

26. A method of producing a radiolabeled MX-DTPA, comprising combining the MX-DTPA composition of claim 25 with a radiolabel.

27. A process for preparing CHx-DTPA comprising:

(a) coupling N-tert-butoxycarbonyl-p-nitro-L-phenylalanine (A) and mono protected diamine (B") to form compound (C");

(b) removing the amine protecting groups in (C") to form the TFA-salt (D");

(c) reducing (D") to form (E");

(d) penta-alkylating (E") to form (F");

(e) removing the amine protecting groups in (F") to form the trifluoroacetic acid salt (G");

(f) reducing the nitro group in (G") to form the trifluoroacetic acid salt (H"); and (g) converting the amino group in (H") to form the CHx-DTPA.

28. The process of claim 27, wherein the mono protected diamine (B") is in the sys form.

29. The process of claim 27, wherein the mono protected diamine (B") is in the trans form.

* * * * *